(12) United States Patent
Kim et al.

(10) Patent No.: US 11,725,640 B2
(45) Date of Patent: *Aug. 15, 2023

(54) ELECTROOSMOTIC PUMP

(71) Applicant: EOFLOW CO., LTD., Seongnam-si (KR)

(72) Inventors: Seung Ha Kim, Goyang-si (KR); Jae Hong Kim, Namyangju-si (KR); Jesse Jaejin Kim, Seongnam-si (KR); Yongchul Song, Seongnam-si (KR)

(73) Assignee: EOFLOW CO., LTD., Seongnam-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/652,139

(22) Filed: Feb. 23, 2022

(65) Prior Publication Data

US 2022/0170447 A1 Jun. 2, 2022

Related U.S. Application Data

(63) Continuation of application No. 16/326,768, filed as application No. PCT/KR2017/008292 on Aug. 1, 2017, now Pat. No. 11,286,918.

(30) Foreign Application Priority Data

Aug. 31, 2016 (KR) .................. 10-2016-0112131

(51) Int. Cl.
*F04B 19/00* (2006.01)
*A61M 39/24* (2006.01)
(Continued)

(52) U.S. Cl.
CPC .......... *F04B 19/006* (2013.01); *A61M 5/142* (2013.01); *A61M 5/145* (2013.01); *A61M 39/24* (2013.01);
(Continued)

(58) Field of Classification Search
CPC .......... F04B 17/00; F04B 17/03; F04B 19/00; F04B 19/006; F04B 43/02; F04B 43/04;
(Continued)

(56) References Cited

U.S. PATENT DOCUMENTS 4,903,655 A 2/1990 Vonderau et al.
2006/0013710 A1 1/2006 Lee
(Continued)

FOREIGN PATENT DOCUMENTS

CN 103827487 A 5/2014
EP 3037117 6/2016
(Continued)

OTHER PUBLICATIONS

Author: Lister et al. Title: A two-liquid electroosmotic pump using low applied voltage and power Date published (mm/dd/yyyy): Jul. 18, 2010 Date accessed (mm/dd/yyyy): Nov. 28, 2022 Link: https://www.sciencedirect.com/science/article/pii/S0924424710003 1717via%3Dihub (Year: 2010).*

(Continued)

*Primary Examiner* — Charles G Freay
*Assistant Examiner* — Chirag Jariwala
(74) *Attorney, Agent, or Firm* — Knobbe, Martens, Olson & Bear, LLP

(57) ABSTRACT

The present invention discloses a path-type liquid medicine delivery electro-osmosis pump that can be applied to a wearable medicine device.
An electro osmosis pump according to the present invention includes: a connector provided with a liquid medicine inlet and a liquid medicine outlet; a check valve assembly combined to one side of the connector; and a driver that is connected to the other side of the connector and moves the liquid medicine toward the liquid medicine outlet by apply- (Continued)

ing pressure to the liquid medicine while being separated from the liquid medicine, which passes through the check valve assembly.

13 Claims, 5 Drawing Sheets

(51) Int. Cl.
*A61M 5/142* (2006.01)
*A61M 5/145* (2006.01)
(52) U.S. Cl.
CPC ....... *F04B 19/00* (2013.01); *B01L 2400/0418* (2013.01)
(58) Field of Classification Search
CPC ...... F04B 43/043; F04B 43/06; F04B 43/067; F04B 53/10; F04B 53/1037; F04B 53/16; A61M 5/142; A61M 5/145; A61M 2005/14204; A61M 2005/14513; B01L 3/5027; B01L 2400/0418; B01L 2200/027
USPC ......................................................... 417/48
See application file for complete search history.

(56) References Cited

U.S. PATENT DOCUMENTS

| | | |
|---|---|---|
| 2006/0264835 A1 | 11/2006 | Nielsen et al. |
| 2007/0021735 A1 | 1/2007 | Bhavaraju et al. |
| 2011/0180464 A1 | 7/2011 | Schmitt |
| 2016/0177931 A1 | 6/2016 | Shin et al. |
| 2018/0056663 A1* | 3/2018 | Asawa .................... F04B 53/10 |

FOREIGN PATENT DOCUMENTS

| | | |
|---|---|---|
| JP | 52-083007 | 6/1977 |
| JP | 2006/200524 A | 8/2006 |
| JP | 2006/300037 A | 11/2006 |
| JP | 2009/500078 A | 1/2009 |
| JP | 2013/521885 A | 6/2013 |
| JP | 2015/203310 A | 11/2015 |
| KR | 10-2011-0048162 | 5/2011 |
| KR | 10-2013-0081874 | 7/2013 |
| KR | 10-1420360 | 7/2014 |
| WO | WO 2006/068263 A1 | 6/2006 |
| WO | WO 2007/005565 A2 | 7/2007 |
| WO | WO 2011/112723 | 9/2011 |
| WO | WO 2012/151581 A1 | 8/2012 |

OTHER PUBLICATIONS

Author: Lister et al. Title: A two-liquid electroosmotic pump using low applied voltage and power Date published (mm/dd/yyyy): Jul. 18, 2010 Date Accessed (mm/dd/yyyy): May 26, 2020 Link: http://microfluidlcs.stanford.edu/Publications/Micropumps_Cooling/Lister-Two-Liquid-EO-Pump.pdf (Year: 2010).

Chinese Office Action for Chinese Patent Application No. 201780052756.2, dated Sep. 27, 2020 in 15 pages including English Translation.

Extended Search Report dated Jan. 15, 2020 in European Patent Application No. 1786852; 7 pages.

Office Action dated Jan. 28, 2020 in Japanese Patent Application No. 2019-511604; 6 pages.

* cited by examiner

ELECTROOSMOTIC PUMP

CROSS-REFERENCE TO RELATED APPLICATIONS

This application is a continuation of U.S. application Ser. No. 16/326768, filed on Feb. 20, 2019, as the U.S. National Phase under 35 U.S.C. § 371 of International Application PCT/KR2017/008292, filed Aug. 1, 2017, which claims priority to Korean Patent Application No. 10-2016-0112131, filed Aug. 31, 2016. Each of these applications is hereby incorporated by reference in its entirety.

TECHNICAL FIELD

The present invention relates to a patch-type liquid medicine delivery device attached to a human body or an electro-osmosis pump for transmission of liquid medicine, which may be applied to a wearable medical device.

BACKGROUND ART

An electro-osmosis pump is a pump that uses a phenomenon of fluid movement which occurs when a voltage is applied to opposite ends of a capillary or a porous separation membrane. The electro-osmosis pump can be manufactured to be very small in size compared to a general mechanical pump, and generates no noise and consumes less power.

For example, international patent publication No. WO 2011/112723 discloses an electro osmosis pump that includes a ceramic membrane disposed between a porous sliver/oxidized silver anode and a porous sliver/oxidized cathode.

The above-stated patent discloses a liquid medicine delivery device in which electrodes are formed at opposite ends of the ceramic separation membrane, and when a predetermined potential is applied to the electrodes, a pressure that corresponds to the corresponding potential is generated and the device uses the pressure. The liquid medicine delivery device additionally uses two electric fluid chambers and a needle for injection of liquid medicine.

However, the electro osmosis pump used in the liquid medicine delivery device has a structure in which liquid medicine to be delivered and water, which is an operation fluid used for driving of the pump are separated from each other by oil, and thus unexpected mixing of the liquid medicine and water may occur at any time in an interface between the liquid medicine and water.

In the electro osmosis pump, liquid medicine, which is an object to be delivered, and water, which is an operation fluid, need to be separated from each other. Liquid medicine is a mixture of various substances, and a biologically active substance in components of the mixture may be oxidized or reduced in a potential for driving of the electro osmosis pump. In addition, when the liquid medicine directly contacts the electrode, a high molecular substance such as protein is adsorbed to the electrodes, thereby deteriorating performance of the pump, and accordingly, it is preferable that the electrodes and the liquid medicine need to be separated from each other. However, a conventional method cannot sufficiently satisfy such a condition.

In addition, an amount of power to be consumed for driving of the pump is a factor that determines practical utility when the pump is applied to a patch-type liquid medicine delivery device or a wearable medical device attached to a human body, and accordingly, a small-sized pump, which can be driven with low power, is required.

DISCLOSURE

Technical Problem

The present invention has been made in an effort to resolve the above-described problems, and provides an electro osmosis pump that can be stably driven by preventing liquid medicine, which is an object to be delivered, and operation fluid from being mixed with each other, thereby improving merchantability, and can prevent a side effect thereby the therapeutic effect for a patient.

In addition, another purpose of the present invention is to provide an electro osmosis pump that can maximize fluid transfer efficiency with respect to power consumption.

Technical Solution

In order to achieve such a purpose, the present invention provides an electro osmosis pump that includes: a connector provided with a liquid medicine inlet and a liquid medicine outlet; a check valve assembly combined to one side of the connector; and a driver that is connected to the other side of the connector and moves the liquid medicine toward the liquid medicine outlet by applying pressure to the liquid medicine while being separated from the liquid medicine, which passes through the check valve assembly.

The check valve assembly may include: an inflow check valve that is disposed in the liquid medicine inlet to move the liquid medicine in one direction; and an discharge check valve that is disposed in the liquid medicine outlet to discharge the liquid medicine delivered through the inflow check valve.

It is preferable that the check valve assembly is combined to the connector and includes a liquid medicine inflow extension pipeline and a liquid medicine discharge extension pipeline, the liquid medicine inflow extension pipeline is connected to the liquid medicine inlet and the liquid medicine discharge extension pipeline is connected to the liquid medicine outlet, and an inflow check valve is disposed in the liquid medicine discharge extension pipeline and a discharge check valve is disposed in the liquid medicine discharge extension pipeline.

It is preferable that a first fixing hole that fixes the inflow check valve is formed in the liquid medicine inflow extension pipeline, and a second fixing hole that fixes the discharge check valve is formed in the liquid medicine discharge extension pipeline.

It is preferable that the driver includes: a first diaphragm that is combined to the connector and blocks liquid medicine of the check valve assembly; a first pump housing that is combined to the first diaphragm and provided with a space where an operation fluid is received; a first power supply line that is combined to the first pump housing and receives power; a first electrode connected to the first power supply line; a membrane of which one side is combined to the first electrode; a second electrode combined to the other side of the membrane; a second power supply line that supplies power to the second electrode; a second pump housing combined to one side of the second electrode and provided with a space where an operation fluid is received; and a second diaphragm combined to the second pump housing.

It is preferable that the first pump housing is provided with a space that penetrates along an axial direction and the space of the first pump housing is blocked by the first diaphragm and the first electrode, and the second pump housing is provided with another space that penetrates along the axial direction and the space of the second pump housing is blocked by the second electrode and the second diaphragm.

It is preferable that a space in which liquid medicine is introduced into through the liquid medicine inlet and discharged through the liquid medicine inlet is formed between the connector and the first diaphragm.

It is preferable that the membrane is formed of a porous material through which an operation fluid and ions can be transferred.

The membrane is preferably formed of an insulator.

It is preferable that the first diaphragm or the second diaphragm is provided with a wrinkle portion that is formed as protrusions and depressions.

Advantageous Effects

According to the present invention, a pump operation fluid and a fluid to be delivered such as liquid medicine are separated from each other by a flexible diaphragm and thus an active component included in the fluid to be delivered can be prevented from being spoiled due to an electro-chemical reaction by a voltage applied to an electrode.

In addition, according to the present invention, a component included in the pump operation fluid can be prevented from being fixed with the liquid medicine, and thus various transfer fluids can be applied in design of a patch-type liquid medicine delivery device, thereby increasing the degree of freedom in a design. That is, the present invention enables the design of a patch-type liquid medicine delivery device that can selectively supply an optimum liquid medicine to a patient suffering from a specific disease such as diabetes, or can be applied to patients suffering from various diseases.

Further, the present invention provides an effect of improving merchantability of the electro osmosis pump driven with low power and high efficiency by applying a check value having a very low opening pressure and increasing a reaction speed of the check value.

MODE FOR INVENTION

Figure 1:
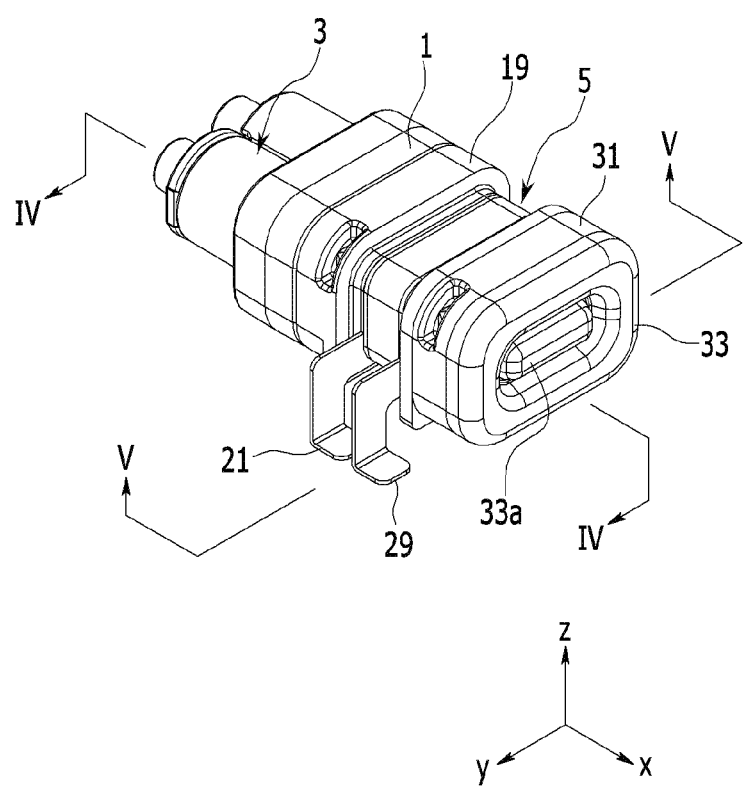
FIG. 1 is a perspective view of an external appearance of an electro osmosis pump provided for description of an exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 2:
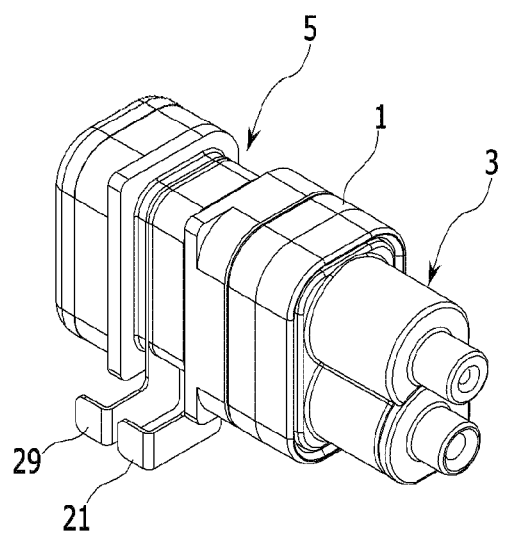
FIG. 2 is a perspective view of the electro osmosis pump of FIG. 1, viewed from a different angle.
Figure 2:
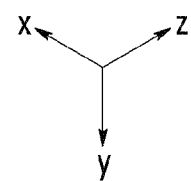
Figure 3:
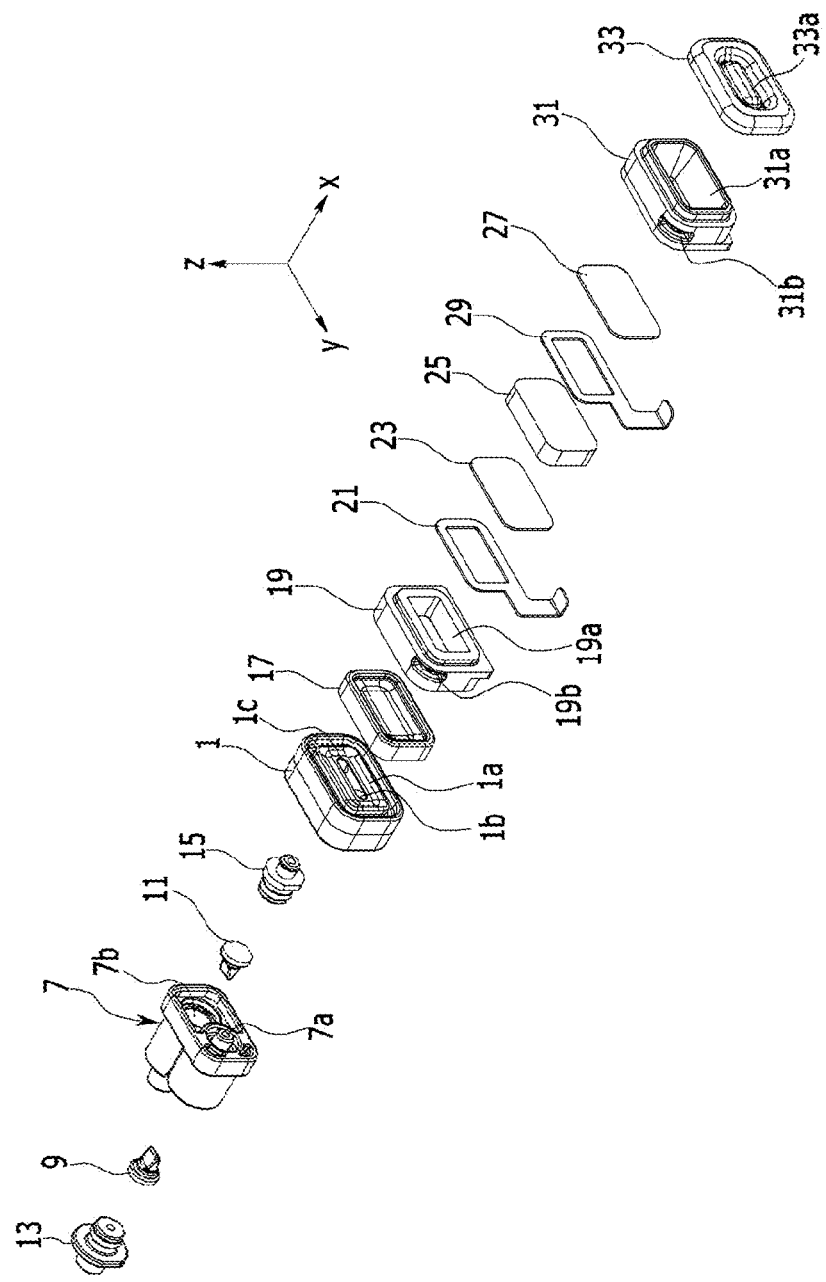
FIG. 3 is an exploded perspective view of FIG. 1.
Figure 4:
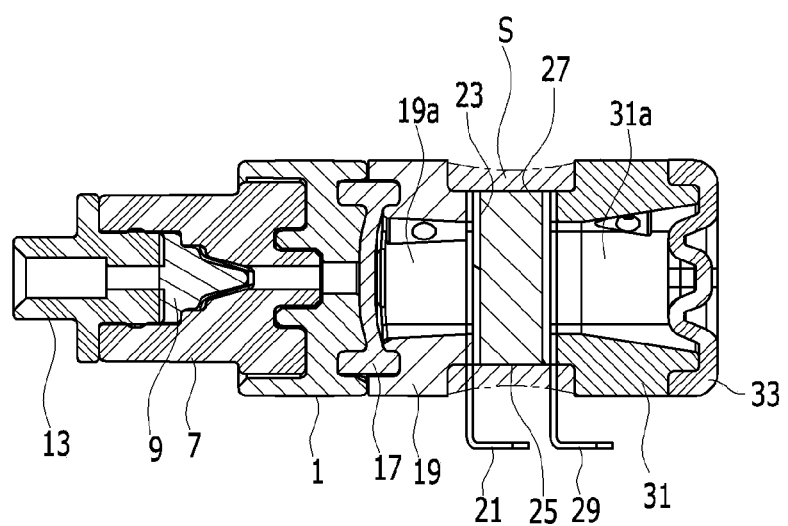
FIG. 4 is a cross-sectional view of FIG. 1, taken along the line IV-IV.
Figure 5:
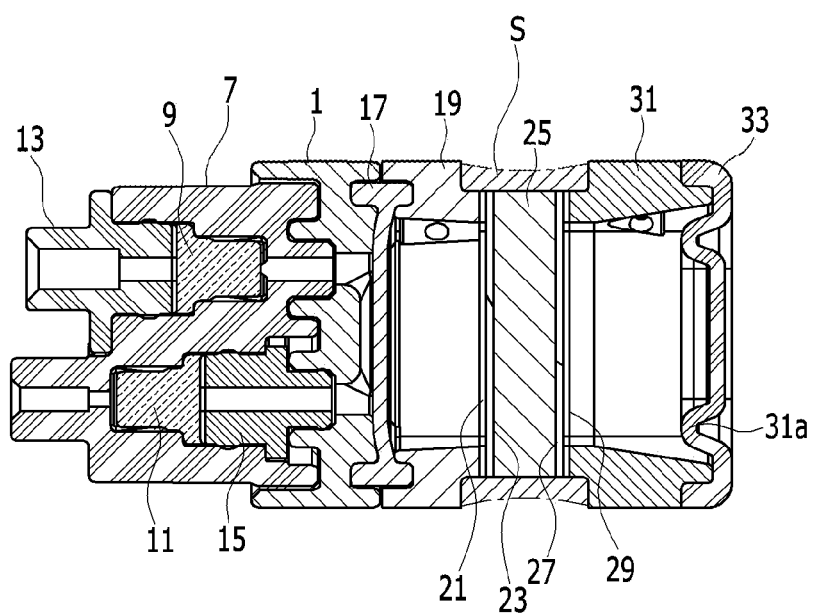
FIG. 5 is a cross-sectional view of FIG. 1, taken along the line V-V.

FIG. 1 and FIG. 2 are perspective view provided for description of an exemplary embodiment of the present invention, FIG. 3 is an exploded perspective view of FIG. 1, FIG. 4 is a cross-sectional view of FIG. 1, taken along the line IV-IV, and FIG. 5 is a cross-sectional view of FIG. 1, taken along the line V-V, which illustrates an electro-osmosis pump.

An electro-osmosis pump according to an exemplary embodiment of the present invention includes a connector 1, a check valve assembly 3, and a driver 5.

The check valve assembly 3 may be combined to one side of the connector 1 and the driver may be combined to the other side of the connector 1. The connector 1 is provided with a barrier rib 1a that partitions the check valve assembly 3 and the driver 5. The barrier rib 1a includes a liquid medicine inlet 1b and a liquid medicine outlet 1c.

The liquid medicine inlet 1b and the liquid medicine outlet 1c are disposed at a distance from each other, and penetrate the barrier rib 1a.

Liquid medicine to be injected into a human body is put into the liquid medicine inlet 1b, and the liquid medicine outlet 1c may be a path through which the liquid medicine put into the liquid medicine inlet 1b is discharged so as to be injected back into the human body.

The check valve assembly 3 may include a valve housing 7, an inflow check valve 9, a discharge check valve 11, a first fixing hole 13, and a second fixing hole 15.

The valve housing 7 includes a liquid medicine inflow extension pipeline 7a and a liquid medicine discharge extension pipeline 7b. The valve housing 7 may be combined to one side of the connector 1. In addition, the liquid medicine inflow extension pipeline 7a is connected to the liquid medicine inlet 1b, and the liquid medicine discharge extension pipeline 7b is connected to the liquid medicine outlet 1c.

The inflow check valve 9 is disposed in the liquid medicine inflow extension pipeline 7a. The inflow check valve 9 may let liquid medicine injected into a human body pass to the liquid medicine inlet 1b and block movement of the liquid medicine in the reverse direction.

The discharge check valve 11 is disposed in the liquid medicine discharge extension pipeline 7b. The discharge check valve 11 may let the liquid medicine passed through the liquid medicine inlet 1b pass in a direction of injection into the human body, and blocks movement in the reverse direction.

As the inflow check valve 9 and the discharge check valve 11, duckbill valves that are flexible and have a low open-pressure may be used. Fluid transmission efficiency compared to a power consumption amount is increased by the inflow check valve 9 and the discharge check valve 11, thereby enabling long-time operation and improving productivity.

The first fixing hole 13 is fitted into the liquid medicine inflow extension pipeline 7a to fix the inflow check valve 9. The second fixing hole 15 is fitted into the liquid medicine discharge extension pipeline 7b to fix the discharge check valve 11.

In addition, the first fixing hole 13 and the second fixing hole 15 preferably have pipelines through which liquid medicine can pass.

In the exemplary embodiment of the present invention, the inflow check valve 9 and the discharge check valve 11 are combined to the valve housing 7, but this is not restrictive, and the inflow check valve 9 and the discharge check valve 11 may be respectively combined to the liquid medicine inlet 1b and the liquid medicine outlet 1c provided in the connector 1. In this case, the valve housing 7 is integrally formed with the connector 1 so that it can be manufactured with a simpler structure. According to the other exemplary embodiment of the present invention, the number of parts is reduced so that manufacturing cost can be more saved, and the product can be manufactured to be more compact.

The driver 5 is combined to one side of the connector 1. The driver 5 is preferably disposed opposite to a side where the check valve assembly 3 is combined. The driver 5 is preferably disposed apart from the liquid medicine that passes through the check valve assembly 3. The driver 5 applies pressure to the liquid medicine passed through the check valve assembly 3 such that the liquid medicine can pass through the liquid medicine outlet 1c.

The driver 5 may include a first diaphragm 17, a first pump housing 19, a first power supply line 21, a first electrode 23, a membrane 25, a second electrode 27, a second power supply line 29, a second pump housing 31, and a second diaphragm 33.

The first diaphragm 17 is combined to one side of the connector 1. A space is provided between the first diaphragm 17 and the connector 1. That is, the first diaphragm 17 is combined to the connector 1, while maintaining a certain space in the connector 1. Thus, liquid medicine at the check valve assembly 3 maintains a state of being isolated rather than moving toward the driver 5 by the first diaphragm 17.

The first diaphragm 17 of which a plane that forms the first diaphragm 17 can iteratively move in a predetermined section in an axial direction by a pressure generated from the driver 5. A wrinkle portion may be provided in the first diaphragm 17 to allow the plane to smoothly move along the axial direction (i.e., the x-axis direction in FIG. 1).

The first diaphragm 17 is combined to one side of the first pump housing 19. The first pump housing 19 is provided with a space 19a that penetrates along an axial direction. Thus, one side of the space 19a of the first pump housing 19 may be closed by the first diaphragm 17.

The first electrode 23 is combined to the other side of the first pump housing 19 so that the space 19a formed by the first pump housing 19 may be closed. In addition, the first pump housing 19 may accommodate operation fluid such as water and the like in the space 19a provided therein.

The first pump housing 19 may be provided with a fluid injection hole portion 19b at an external circumference thereof. Such a hole portion 19b may be sealed after the operation fluid is injected into the first pump housing 19. Thus, the operation fluid of the driver 5 may be separated from the liquid medicine at the check valve assembly 3.

The first power supply line 21 may supply power to the first electrode 23. The first power supply line 21 is disposed along an edge of the first pump housing 19, and may be fixed to the first electrode 23 by contacting the same. The first power supply line 21 is preferably disposed between the first pump housing 19 and the first electrode 23. However, according to another exemplary embodiment of the present invention, the first power supply line 21 may supply power to the first electrode 23, and may be disposed between the first electrode 23 and the membrane 25.

The first electrode 23 is formed in the shape of a plate and thus may close the space 19a of the first pump housing 19. That is, the first pump housing 19 may form the space 19a with the first diaphragm 17 and the first electrode 23. In addition, the operation fluid such as water and the like is accommodated in the space 69a of the first pump housing 19.

The membrane 25 may be formed of a porous material through which the operation fluid and ions can be transferred. The membrane 25 is preferably made of an insulator such as a ceramic and the like. When the membrane 25 is formed of an insulator, an electro-chemical reaction material used in the first electrode 23 and the second electrode 27 is consumed or desorbed due to long-term driving of the electro-osmosis pump and thus the porous membrane 25 is exposed. However, in this case, even when conventional carbon paper or carbon cloth is used, a side reaction such as electrolysis of water, which occurs due to exposure to carbon paper or carbon cloth, does not occur. Thus, unnecessary power consumption due to a side reaction can be prevented. Therefore, according to the present invention, a safe driving characteristic can be provided and durability can be improved.

The membrane 25 may be used by processing a flexible non-conductive material such as a polymer resin, rubber, urethane, or a plastic film into a thin film form.

The second electrode 77 is disposed at the other side of the membrane 75. That is, the membrane 25 is preferably disposed between the first electrode 23 and the second electrode 27. The second power supply line 29 may supply external power to the second electrode 27. The second power supply line 29 may be combined to an edge of the second pump housing 31. However, the second power supply line 29 may have any alignment structure as long as it has a structure for supplying power to the second electrode 27.

The shape of the second pump housing 31 is the same as or similar to the shape of the first pump housing 19. Another space 31a that penetrates the second pump housing 31 along an axial direction is provided in the second pump housing 31. As in the first pump housing 19, a hole portion 31b that penetrates the space 31a may be provided in the second pump housing 31. The hole portion 31b of the second pump housing 31 may be sealed by a sealant or filled by welding and the like after operation fluid is injected therein.

The second diaphragm 33 is combined to one side of the second pump housing 31 and thus may close the space 31a provided in the second pump housing 31.

That is, the second pump housing 31 may close the space 31a by using the second electrode 27, which is formed in the shape of a plate, and the second diaphragm 33.

A wrinkle portion 33a may be formed in a plane of the second diaphragm 33. The wrinkle portion 33a formed in the second diaphragm 33 may be formed of protrusions and depressions that protrude in the axial direction with reference to a cross-section. The wrinkle portion 33a of the second diaphragm 33 enhances performance of pumping by sufficiently moving the plane of the second diaphragm 33 along the axial direction.

In the exemplary embodiment of the present invention, the wrinkle portion 33a is formed in the second diaphragm 33, but depending on exemplary embodiments, a wrinkle portion may be also formed in the first diaphragm 17. In addition, a wrinkle portion that can be formed in the first diaphragm 17 or the second diaphragm 33 maximizes deformation of the first diaphragm 17 and the second diaphragm 33 with small energy, thereby reducing energy consumption. That is, the driver 5 can be driven for a long period of time with a small external power source.

As shown in FIG. 4 and FIG. 5, the above-described first pump housing 19, the first power supply line 21, the first electrode 23, the membrane 25, the second electrode 27, the second power supply line 29, and the second pump housing 31 may be air-tightly sealed from the outside by an encapsulant S. That is, the first power supply line 21, the first electrode 23, the membrane 25, the second electrode 27, and the second power supply line 29 are formed relatively smaller than the first pump housing 19 and the second pump housing 31 in size, and thus the encapsulant S may be disposed in a circumferential portion (i.e., a portion exposed to the outside and a portion that forms a groove or a space with reference to a cross-section) between the first pump housing 19 and the second pump housing 31 while the first power supply line 21, the first electrode 23, the membrane 25, the second electrode 27, and the second power supply line 29 are in an assembled state. Such an encapsulant S may form an encapsulation layer that maintains air-tight encapsulation from the outside.

As the encapsulant, an adhesive such as a hot melt adhesive, an epoxy adhesive, a polyurethane adhesive, or a cyanoacrylate adhesive may be used. However, the encapsulant is not limited to such examples, and any material that is rigidly cured to prevent leakage of operation fluid and prevent deformation of an external appearance of a configuration element is applicable.

An operation process of the above-described exemplary embodiment of the present invention will now be described in detail.

First, power is supplied such that the first power supply line 21 and the second power supply line 29 have different polarities, and a voltage difference occurs between the first electrode 23 and the second electrode 27. Due to such a voltage difference, positive ions are generated as a result of an electrode reaction in an anode. The positive ions generated from the above-stated reaction move to a cathode and pass through the membrane 25 while pulling the operation fluid together such that a pressure (a pumping force) is generated.

That is, such an electrochemical reaction enables ions and the operation fluid to move to the space 19a of the first pump housing 19 or the space 31a of the second pump housing 31 by passing through the membrane 25.

When the polarity of power of the first electrode 23 and the polarity of power of the second electrode 27 are alternately supplied through the first power supply line 21 and the second power supply line 29, the operation fluid can be iteratively moved to the space 69a of the first pump housing 19 and the space 31a of the second pump housing 31 by the above-described electrochemical reaction.

That is, when an electrode which functions as an anode is changed to serve as a cathode due to alternation of the voltage polarity, an electro-chemical reactant consumed when the electrode is used as an anode can be recovered when the electrode is used as a cathode, and vice versa. Accordingly, the electro-osmosis pump can be continuously driven.

Then, the first diaphragm 17 and the second diaphragm 33 are deformed and a pressure is generated. Such a pressure is applied to a space between the connector 1 and the first diaphragm 17.

Then, the liquid medicine is introduced into the liquid medicine inlet 1b through the liquid medicine inflow extension pipeline 7a by the pressure. The introduced liquid medicine may be injected into a human body while being discharged along the liquid medicine outlet 1c and the liquid medicine discharge extension pipeline 7b.

In this case, the inflow check valve 9 and the discharge check valve 11 allow the liquid medicine to move along only one direction. Thus, the electro-osmosis pump according to the exemplary embodiment of the present invention can safely inject liquid medicine into a human body while using low power.

In particular, since the operation fluid of the driver 5 and the liquid medicine are separated from each other, the electro-osmosis pump 5 of the exemplary embodiment of the present invention can prevent an active component included in the liquid medicine from being spoiled due to an electrochemical reaction.

In addition, according to the present invention, a component included in the operation fluid of the driver 55 can be prevented from being transmitted to the liquid medicine such that a wider range of liquid medicine or operation fluid is applicable.

In addition, according to the present invention, a check valve of which an opening pressure is very low is used so that a reaction speed of the check valve is very fast, and accordingly, the pump can be driven with low power and high efficiency as a whole.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A patch-type liquid medicine delivery device configured to attach to a human body, the device comprising:
    a driver configured to move a liquid medicine toward the human body by applying pressure to the liquid medicine; and
    a check valve assembly coupled to the driver, wherein the liquid medicine pushed by the driver passes through the check valve assembly,
    wherein the driver comprises:
        a first pump housing provided with a space where an operation fluid is received;
        a first electrode;
        a membrane of which one side is combined to the first electrode;
        a second electrode combined to other side of the membrane;
        a second pump housing combined to one side of the second electrode and provided with a space where the operation fluid is received; and
        a diaphragm combined to the first pump housing,
    wherein the check valve assembly comprises:
        a valve housing comprising a liquid medicine inflow extension pipeline and a liquid medicine discharge extension pipeline;
        an inflow check valve passing the liquid medicine toward the driver;
        a discharge check valve passing the liquid medicine in a direction of injection into the human body;
        a first fixing hole fixing the inflow check valve to the valve housing; and
        a second fixing hole fixing the discharge check valve to the valve housing,
        wherein the liquid medicine inflow extension pipeline of the valve housing is disposed between the driver and the inflow check valve,
        wherein the second fixing hole is disposed between the driver and the discharge check valve, and
        wherein one end of the first fixing hole in an axial direction is fitted to the liquid medicine inflow extension pipeline of the valve housing and other end of the first fixing hole in the axial direction is exposed to the outside and is not coupled to the driver.

2. The device of claim 1, wherein the membrane is formed of an insulator.

3. The device of claim 1, wherein the diaphragm is provided with a wrinkle portion that is formed as protrusions and depressions.

4. The device of claim 1, wherein the inflow check valve passes the liquid medicine toward the diaphragm of the driver.

5. The device of claim 1, wherein the diaphragm of the driver pushes the liquid medicine toward the check valve assembly.

6. The device of claim 1, wherein one end of the second fixing hole in the axial direction is fitted to the liquid medicine discharge extension pipeline of the valve housing and other end of the second fixing hole in the axial direction is coupled to the driver.

7. The device of claim 1, wherein the membrane is formed of a porous material through which an operation fluid and ions are transferred.

8. The device of claim 1, wherein the space of the first pump housing and the space of the second pump housing penetrate along the axial direction, wherein the space of the first pump housing is blocked by the diaphragm.

9. The device of claim 1 further comprising:
a connector provided with a liquid medicine inlet and a liquid medicine outlet,
wherein the connector is disposed between the driver and the check valve assembly.

10. The device of claim 9, wherein a space in which the liquid medicine is introduced into through the liquid medicine inlet and discharged through the liquid medicine outlet is formed between the connector and the driver.

11. The device of claim 1, wherein the driver further comprises a second diaphragm combined to the second pump housing.

12. The device of claim 11, wherein the space of the first pump housing and the space of the second pump housing penetrate along the axial direction, wherein the space of the second pump housing is blocked by the diaphragm.

13. The device of claim 11, wherein the diaphragm is provided with a wrinkle portion that is formed as protrusions and depressions.

* * * * *